United States Patent [19]

Pless et al.

[11] Patent Number: 4,880,005
[45] Date of Patent: Nov. 14, 1989

[54] PACEMAKER FOR DETECTING AND TERMINATING A TACHYCARDIA

[75] Inventors: Benjamin D. Pless, Palo Alto; Michael B. Sweeney, Mountain View, both of Calif.

[73] Assignee: Intermedics, Inc., Angleton, Tex.

[21] Appl. No.: 198,614

[22] Filed: May 23, 1988

Related U.S. Application Data

[63] Continuation of Ser. No. 765,047, Aug. 12, 1985, abandoned.

[51] Int. Cl.$^4$ ............................................. A61N 1/36
[52] U.S. Cl. .............................. 128/419 PG; 128/705
[58] Field of Search ............. 128/419 PG, 419 D, 705

[56] References Cited

U.S. PATENT DOCUMENTS

| | | | |
|---|---|---|---|
| 4,280,502 | 7/1981 | Baker, Jr. et al. | 128/419 PG |
| 4,312,356 | 1/1982 | Sowton et al. | 128/419 PG |
| 4,398,536 | 8/1983 | Nappholz et al. | 128/419 PG |
| 4,403,614 | 9/1983 | Engle et al. | 128/419 D |
| 4,406,287 | 9/1983 | Nappholz et al. | 128/419 PG |
| 4,408,606 | 10/1983 | Sparrell et al. | 128/419 PG |
| 4,427,011 | 1/1984 | Sparrell et al. | 128/419 PG |
| 4,475,551 | 10/1984 | Langer et al. | 128/419 D |
| 4,523,595 | 6/1985 | Zibell | 128/419 D |
| 4,541,430 | 9/1985 | Elmquist et al. | 128/419 PG |
| 4,577,633 | 3/1986 | Berkovits et al. | 128/419 PG |
| 4,726,380 | 2/1988 | Vollmann et al. | 128/419 PG |

FOREIGN PATENT DOCUMENTS

2121288 12/1983 United Kingdom ............ 128/419 D

OTHER PUBLICATIONS

"RBM Revue Europeene De Technologie Biomedicale", Vol. 6, No. 3, p. 213, May–June, 1984.
Fischer et al., "Maximal Rate of Tachycardia Development: Sinus Tachycardia Development: Sinus Tachycardia with Sudden Exercise Versus Spontaneous Ventricular Tachycardia", *Pace*, Vol. 6, pp. 221–228 (1983).
Waldo et al., "Relevance of Electrograms and Transcient Entrainment for Antitachycardia Devices", *Pace*, Vol. 7, pp. 588–600 (1984).

*Primary Examiner*—Francis Jaworski
*Attorney, Agent, or Firm*—John R. Merkling

[57] ABSTRACT

A heart pacemaker detects pace-terminable tachycardia conditions in the atrium of the heart in accordance with selected high rate, rate stability, sudden onset and sustained high rate criteria. When a pace-terminable tachycardia is detected, programmed treatment modalities are applied to attempt to terminate the tachycardia. The tachycardia is treated by applying timed bursts of electrical pulses in formats defined by programmed primary and secondary treatment modalities. The primary and secondary treatments may be applied in an order which is dependent upon the prior successful treatment of similar tachycardias. The pacemaker may also utilize remembered treatment values which were successfully applied to treat similar tachycardias. The pacemaker may be programmed to restart the primary and secondary modes of treatment in the event that the modes initially failed to terminate a tachycardia. The pacemaker may also be programmed to limit the rate of burst pulses to avoid overstimulating the heart.

38 Claims, 3 Drawing Sheets

Microfiche Appendix Included
(1 Microfiche, 47 Pages)

PACEMAKER FOR DETECTING AND TERMINATING A TACHYCARDIA

This is a continuation of co-pending application Ser. No. 765,047 filed on Aug. 12, 1985 now abandoned.

A microfiche appendix of a computer listing comprising one microfiche with forty-seven total frames is provided pursuant to 37 C.F.R. 1.96(b).

TECHNICAL FIELD

The invention relates to body implantable pacemakers which monitor electrical activity of the heart and stimulate heart tissue as required to revert certain arrhythmias. More particularly, the invention relates to a heart pacemaker which detects a pacer-terminable tachycardia and applies electrical stimulating signals in programmed treatment modalities to terminate the tachycardia.

BACKGROUND OF THE INVENTION

Implantable cardiac pacemakers have been developed to detect undesirably rapid contractions of the heart which are characterized as tachyarrhythmias or tachycardias. It is known that such pacemakers may terminate or interrupt a detected tachycardia by applying stimulation pulses to the heart which coincide with a termination time period for the tachycardia. Such stimulation pulses may be applied in bursts (one or more pulses). In operation, the time at which a burst begins, the number of pulses in the burst and the time interval between such pulses may be programmed to a fixed value or may be adaptively determined as a percentage of the detected rate of the tachycardia. It has also been proposed that the tachycardia treatment pulses may have intervals which automatically decrement within the burst. Alternatively, the time at which the burst begins or the intervals between pulses of the burst may be "scanned" by incrementing and/or decrementing these values by programmed amounts as bursts are applied to terminate a tachycardia.

Typically, antitachycardia pacemakers attempt to terminate tachycardias when the heart rate exceeds a predefined high rate. Although this means for detecting a tachycardia has the advantage of simplicity, it has the disadvantage that it will detect and attempt to treat high rate sinus rhythms which result from exercise and which the pacemaker should not attempt to terminate. Also, use of the simple high rate detection criterion will result in an attempt to treat other non-pace-terminable conditions.

It is therefore desirable to develop detection criteria which can distinguish and treat only those tachycardias which are susceptible to pacer-termination, such as reentrant tachycardias. It has been suggested that a pace-terminable tachycardia may be more accurately identified by detecting the rate of onset of the tachycardia. Suddenness of onset often indicates a reentrant tachycardia which may be treated by the pacemaker. High rate sinus rhythms resulting from exercise will not be detected as pacer-terminable tachycardias, because they do not have the characteristic of sudden onset.

Although the sudden onset detection criterion is useful in distinguishing pacer-terminable tachycardias, it is not capable of discriminating between all such tachycardias. Moreover, a simple sudden onset criterion could mistakenly indicate a pacer-terminable tachycardia as a result of transitory cardiac conditions, such as the compensatory pause that normally follows a premature cardiac contraction occurring during a period of high rate cardiac activity.

It is therefore desirable to provide an improved system for reliably detecting pace-terminable tachycardias. Accordingly, it is an object of the invention to provide a pacemaker which reliably detects pace-terminable tachycardias in accordance with programmed detection criteria which are defined with respect to the needs of a patient.

Another object of the invention is to provide a pacemaker which employs the criteria of high rate, sudden onset, rate stability and sustained high rate to distinguish pace-terminable tachycardia conditions which may be treated.

A further object of the invention is to provide such a pacemaker wherein the criteria may be selectively combined to maximize the probability of detecting pace-terminable tachycardias for a particular patient.

Another object of the invention is to provide a pacemaker with an improved sudden onset tachycardia detection criterion which distinguishes actual pace-terminable tachycardias from transitory cardiac conditions which may occur as a result of a compensatory pause following a premature cardiac contraction during a period of high rate cardiac activity.

A further object of the invention is to provide a pacemaker with a rate stability criterion which compares the present high cardiac rate with an average cardiac rate determined from prior rate measurements and diagnoses a pace-terminable tachycardia if the present rate is within a predefined range of the average rate.

Another object of the invention is to provide a pacemaker with a sustained high rate criterion which will cause a tachycardia to be treated if a predefined high cardiac rate is sustained for a predetermined period, even if other selected cardiac detection criteria have not been met.

It has been suggested that an antitachycardia pacemaker may treat a tachycardia with treatment parameters which were successfully applied to treat a previous tachycardia. Although this general procedure has the advantage, on the average, of reducing the time required to treat successive tachycardias, it has the disadvantage that it may extend the time for treatment by attempting to treat a tachycardia of one rate with treatment modalities which were previously successful in terminating a tachycardia having a very different rate.

It is therefore an object of the invention to provide an antitachycardia pacemaker which remembers the values of the parameters of treatment modalities which were successfully applied to one tachycardia and which applies these remembered values to treat a similar tachycardia.

A further object of the invention is to provide an antitachycardia pacemaker which conditions its use of remembered values of treatment modalities on a comparison of the present tachycardia rate with the tachycardia rate of the previous successfully treated tachycardia.

Another object of the invention is to provide an antitachycardia pacemaker which utilizes primary and secondary methods for treating a tachycardia.

It is a further object of the invention to provide a pacemaker wherein the secondary treatment method may be applied first, if the treatment history indicates that this method has been more successful than the primary method for treating a similar tachycardia.

Another object of the invention is to provide a pacemaker wherein a detected pace-terminable tachycardia is treated by preselected primary and secondary methods and, if these methods do not terminate the tachycardia, the pacemaker optionally restarts the treatment methods to again attempt to terminate the tachycardia.

These and other objects of the invention will become apparent from a review of the drawings and the detailed description of a preferred embodiment which follows.

SUMMARY OF THE INVENTION

In order to achieve the objects of the invention and to overcome the problems of the prior art, the pacemaker of the invention includes a microprocessor which is programmed to detect a pace-terminable tachycardia by using a detection algorithm which selectively includes high rate, rate stability, sudden onset and sustained high rate tests.

The pacemaker of the invention treats a detected tachycardia by applying electrical stimulating pulses to the heart in programmed treatment modalities. The treatment modalities are defined in terms of the number of stimulating pulses applied to the heart, the time at which the first of such pulses is applied following a detected tachycardia depolarization and the period between stimulating pulses.

The start delay and the pulse-to-pulse interval may be defined as fixed program values, or as adaptive values derived as a percentage of the detected high cardiac rate. If a burst is generated, the start delay of the pulse or the pulse-to-pulse interval of the burst may be "scanned" by incrementing or decrementing the values of these parameters a preselected number of steps or by incrementing and decrementing the parameters in a predefined search pattern. Alternatively, the intervals of the pulses within a burst may be automatically decremented in the autodecremental mode.

In adaptive and autodecremental bursting the period between burst pulses may not be decreased below a predefined programmed minimum interval. This programmed limit helps ensure that the heart will not be stimulated by excessively high rate bursts.

The values of successfully applied burst treatment parameters may be remembered and applied to terminate similar tachycardias which are later detected. At least a primary and an optional secondary treatment modality are employed in an effort to terminate each detected tachycardia. The order of application of the primary and secondary modalities may be reversed if the secondary treatment was the only recorded successful modality for treating a previous similar tachycardia.

If the primary and secondary treatment modalities are unsuccessful in treating a tachycardia, the modalities may be tried again if selected conditional restart criteria are met.

DETAILED DESCRIPTION OF PREFERRED EMBODIMENT

The pacemaker of the invention employs selective detection criteria to detect the presence of a tachyarrhythmia or tachycardia of the heart. When a tachycardia is detected, the pacemaker reacts in a programmed fashion to attempt to terminate the undesirable condition by applying programmed bursts of electrical signals to the heart in accordance with selected treatment modalities. If a detected tachycardia is similar to a previously successfully terminated tachycardia, the pacemaker may be programmed to apply the previous successful treatment modality to terminate the present tachycardia.

In principle, the detection and treatment modalities of the invention may be utilized to detect and treat a tachycardia in the atrium and/or ventricle of the heart. However, the detection and treatment modalities have at present been implemented primarily to detect and terminate supra-ventricular tachycardias. Accordingly, the detection and treatment criteria of the invention will hereafter be described with respect to a single chamber atrial pacemaker. It should be understood that the disclosed single chamber embodiment does not limit the invention to use in the atrium. The invention may be employed to detect and treat tachycardias of the ventricle as well as the atrium.

The pacemaker of an embodiment of the invention can detect atrial reentrant tachycardias. Reentrant tachycardias occur as a result of a circular conduction of electrical signals within the heart. Such tachycardias may be terminated by a properly timed stimulation pulse or set of stimulation pulses which will hereafter be referred to as a "burst". Such tachycardias which can be treated or terminated with antitachycardia pacing are hereafter referred to as pace-terminable tachycardias. Pace-terminable tachycardias must be distinguished from non-pace-terminable heart rhythms which occur, for example as a result of exercise.

It should now be understood that the atrial pacemaker of an embodiment of the invention can more reliably distinguish non-pace-terminable tachycardias such as occur as a result of exercise from pace-terminable tachycardias, for example reentrant tachycardias. If a pace-terminable tachycardia is detected, the pacemaker generates a physician-programmed burst which has previously been efficacious in terminating the tachycardia.

The atrial pacemaker of the invention monitors the operation of the heart by detecting electrical signals or "events" which occur in the atrium. If a periodic atrial signal is not detected, the pacemaker may be programmed to a bradycardia mode to apply an electrical stimulation signal to maintain a predefined pacing rhythm for the heart.

Figure 1:
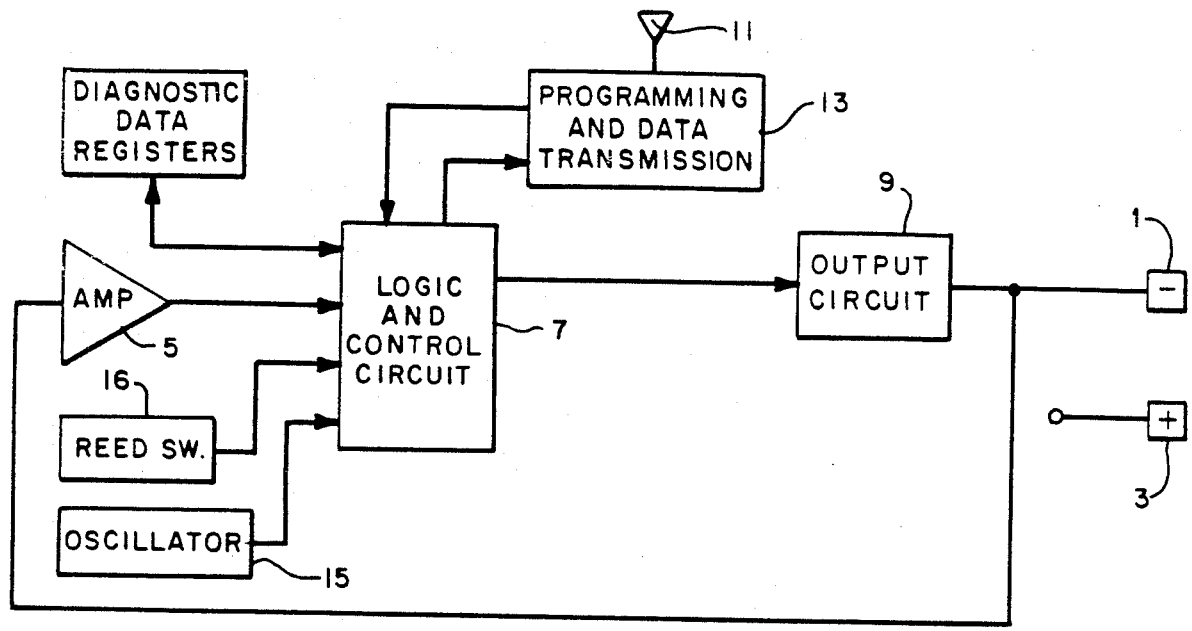
FIG. 1 illustrates a block diagram of the pacemaker of the invention.

FIG. 1 illustrates a block diagram of the major functions of an implanted atrial pacemaker in accordance with the invention. As shown in FIG. 1, the pacemaker includes an atrial tip electrode 1 which contacts the heart (not shown) and an associated ring electrode 3 which provides a ground reference with respect to the electrode 1. These bipolar electrodes apply electrical stimulating signals to the atrium and detect electrical signals which occur within the atrium. Signals detected in the atrium are applied by the electrodes to a sense amplifier 5 which amplifies the signals by frequency-domain filtering if they are within the expected frequency range of cardiac depolarizations. The amplified signals are transmitted to a logic and control circuit 7 which includes a microprocessor. The logic and control circuit includes diagnostic data registers which store digital information concerning the treatment of tachycardias and the detected condition of the heart.

The logic and control circuit of the apparatus of FIG. 1 processes the signals from the sense amplifier 5 and uses time-domain analysis to distinguish between valid cardiac signals and extraneous electrical interference, such as noise signals. The logic and control circuit also generates pacing signals and tachycardia termination bursts which are applied to an output circuit 9 which converts the input logic control signals to voltage levels suitable for stimulating the heart. The pacing or burst signals are applied in accordance with the type of signal that is detected by the sense amplifier 5 and stored treatment information within the microprocessor of the logic and control circuit.

The logic and control circuit implements programmed commands which are received from an external programmer. An implanted antenna coil 11 inductively couples electromagnetic programming pulses from the external programmer to a programming and data transmission circuit 13 which applies the data to the logic and control circuit 7. The received data pulses contain programming information in a pulse-position-modulated, binary-coded format. The binary-coded information is demodulated and stored within the logic and control circuit to define the operating characteristics of the pacemaker.

The timing for the microprocessor and digital circuitry of the pacemaker is provided by a crystal oscillator 15 and certain operational modes are initiated by a reed switch 16 which is actuated by an externally applied magnetic field.

It should generally be understood that the output section 9 of the system of FIG. 1 includes a pulse generator that may be powered, for example by a single 2.8 volt lithum-iodine power cell. The output circuit employs a voltage multiplier and capacitors which are controlled to generate pacing stimuli having a programmed amplitude and timing.

The microprocessor-controlled atrial pacemaker of the invention operates in three bradycardia or atrial pacing modes: AAI, AAT and AOO (ICHD Code). In addition, the pacemaker may be programmed to an OOO or OAO nonpacing mode.

In the AAI or demand inhibited mode the pacemaker of the invention responds to signals detected by the sense amplifier 5 in three ways. First, if atrial depolarizations are not sensed within a predetermined period, the pacemaker generates stimulating pulses at the programmed pacing rate. Second, if spontaneous atrial depolarizations are sensed at a rate higher than the programmed rate, the atrium is not paced. Third, the logic and control circuitry 7 may identify detected signals as electrical interference or noise and initiate either asynchronous pacing at a programmed rate or nonpacing in the 000 mode, depending upon the programmed noise reversion mode of the pacemaker.

In the AAT or demand synchronous mode, the pacemaker paces the heart at a programmed rate in the absence of sensed cardiac depolarizations. The pacemaker also paces the heart synchronously when sensed events occur at or above the programmed rate but below a predetermined maximum pacing rate. Consequently, the pacemaker will not be inhibited in response to extraneous noise sources. If atrial sense events occur so rapidly that the pacemaker would be required to pace faster than its maximum pacing rate, the pacemaker will not pace synchronously with every event. Instead, it will pace synchronously with some events so that the resulting pacing rate is equal to or lower than the predefined maximum pacing rate.

In the AOO or asynchronous mode, the sense amplifier 5 is not used. The pacemaker continuously generates stimulation signals to the heart at a programmed rate.

In the OOO mode, the pacemaker does not pace or sense the heart. In the OAO mode the pacemaker will not pace the heart but does monitor heart activity. These modes may be used to check the patient's heart rhythm without stimulating the heart.

The antitachycardia operation of the pacemaker may be activated in the AAI, AAT or OOO modes without affecting the bradycardia or atrial pacing operation in these modes.

The effectiveness of an automatic antitachycardia pacemaker is significantly increased if the device can distinguish between elevated sinus rhythms, for example resulting from exercise, and pace-terminable rhythms which may occur, for example as a result of reentrant mechanisms. Although a high atrial rate is the most characteristic indicator of a tachycardia, its specificity in identifying pace-terminable tachycardias is limited.

It has been found that pace-terminable tachycardias frequently exhibit characteristics in addition to a high rate. Thus, pace-terminable tachycardias may often be characterized by an abrupt or rapid onset, a relatively stable rate over time, and a high rate sustained over a relatively long period. While pace-terminable tachycardias may occur without these characteristics and sinus rhythm may exhibit them, the characteristics are useful criteria for detecting pace-terminable tachycardias in a majority of cases, and particularly when the criteria are used in combination in the programmable pacemaker of the invention.

Thus, the pacemaker of the invention operates with four programmable detection criteria: high rate, sudden onset, rate stability and sustained high rate. The preferred pacemaker of the invention can combine these criteria in the following nine different combinations to detect the presence of a pace-terminable tachycardia:

1. high rate
2. high rate and sudden onset
3. high rate and (sudden onset or sustained high rate)
4. high rate and rate stability
5. high rate and (rate stability or sustained high rate)
6. high rate and sudden onset and rate stability
7. high rate and [(sudden onset and rate stability) or sustained high rate]
8. high rate and (sudden onset or rate stability)
9. high rate and (sudden onset or rate stability or sustained high rate)

Selection of the appropriate recognition mode for a pace-terminable tachycardia and selection of appropriate numerical values for the parameters of the mode necessitates a complete electrophysiologic analysis of the specific tachycardias being treated. In addition, a study of the patient's normal sinus rhythm is required to determine how best to discriminate a pace-terminable tachycardia for the particular patient.

The high rate criterion of the pacemaker consists of both an interval between successive atrial events and a number of consecutive intervals at or below that selected interval length. In the present embodiment the high rate interval for detecting a tachycardia may be programmed from 266 to 635 msec and the number of consecutive high rate intervals may be programmed from 5 to 99. The requirement that a number of intervals occur sequentially at the defined high rate helps to prevent the pacemaker from responding to short runs of ectopic beats or short excursions over the programmed high rate which may be caused by emotion, exertion, or changes in posture and which therefore should not be treated as pace-terminable tachycardias.

If the pacemaker detects an atrial event which occurs at an interval with respect to the preceding atrial event that is less than the defined high rate interval, the pacemaker will recognize the atrial event as a high rate event. The pacemaker will then count successive high rate events and, if it reaches the programmed number of intervals for the high rate criterion, it will determine that the high rate criterion has been satisfied. However, if the pacemaker detects an interval greater than the programmed high rate interval at any time before having counted the programmed number of high rate intervals, it will begin a new count from zero for the next detected high rate interval.

The sudden onset criterion is programmed for the pacemaker of the invention in terms of the degree of change in successive atrial intervals (i.e., the degree of change in the rate of atrial events). This degree of change is programmable from 20 to 502 msec. The selected value of degree of interval change represents the minimum difference that must exist between a detected high rate interval and a preceding sinus or low rate interval for the pacemaker to diagnose a sudden onset. With this criterion, it should be understood that the larger the value which is selected for the degree of interval change, the more difficult it is to meet sudden onset criterion.

Figure 2:
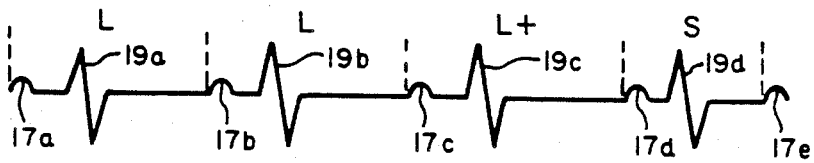
FIG. 2 illustrates a timing diagram of cardiac signals which satisfy the sudden onset tachycardia criterion of the invention.

In operation, the pacemaker records the presently detected high rate atrial interval and then checks the preceding three intervals to determine whether the acceleration in atrial rate was abrupt. The acceleration is identified as abrupt if the immediately preceding interval is longer (i.e., slower rate) than the high rate interval by at least the value of the programmed degree of interval change and either of the next preceding two intervals is longer than the high rate interval. This relationship for detecting a sudden onset is illustrated in FIG. 2. FIG. 2 shows a succession of atrial events 17a–e and corresponding ventricular events 19a–d which occur in time, with the earliest event occurring on the left and the latest or most recent event occurring on the right. The most recent interval between atrial events 17d and 17e is designated as "S" to indicate that this interval is shorter than the predefined high rate interval and therefore corresponds to an atrial rate that is higher than the predefined high rate. As shown in FIG. 2, the intervals between atrial events 17a and 17b and 17b and 17c are characterized as "L", to designate intervals that are longer (slower rate) than the predefined high rate interval. The interval between the atrial events 17c and 17d is designated as "L+", to indicate that this interval is greater than the programmed high rate interval by an amount which exceeds the programmed degree of interval change.

With reference to FIG. 2, the most recent atrial event (17d–e) is recognized as a high rate event, because it occurs with an interval S which is shorter than the predefined high rate interval of the pacemaker. When this high rate interval is detected, the pacemaker checks the next preceding interval and notes that it is longer than the predefined high rate interval by an amount greater than the predefined degree of interval change. The pacemaker then checks the next two preceding intervals and determines that they are both longer ("L") than the defined high rate interval. The pacemaker thus recognizes that the event (17d–e) satisfies the high rate criterion of the pacemaker. It should be understood in this regard that the pacemaker would recognize this event (17d–e) as a sudden onset event as long as either of the intervals defined between the events 17a and b or 17b and c was longer than the high rate interval.

Figure 3:
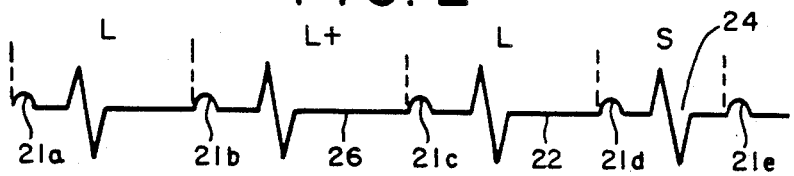
FIG. 3 illustrates other cardiac signals which satisfy the sudden onset criterion of the invention.

FIG. 3 illustrates an example of another sequence of intervals which would be recognized as a sudden onset condition. FIG. 3 illustrates a circumstance wherein the interval 22 just preceding the first detected high rate interval 24 does not satisfy the degree of interval change criterion, but the next preceding interval 26 does satisfy this criterion. Under this circumstance, a sudden onset is detected. Thus, with respect to the atrial events 21a–e, the pacemaker notes that the event 21e occurs at an interval 24 shorter than the predefined high rate interval and therefore recognizes the event 21e as a high rate event. The pacemaker thereafter checks the preceding interval 22 and determines that, although the interval is longer than the defined high rate interval, it does not exceed the high rate interval by the predefined degree of interval change. The pacemaker then checks the next preceding interval 26 and determines that this interval exceeds the high rate interval by at least the defined degree of interval change. The pacemaker thus determines that the high rate event 21e satisfies the sudden onset criteria.

Figure 4:
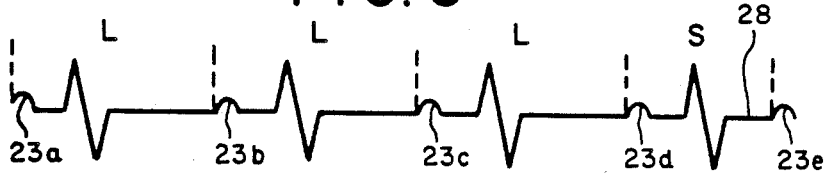
FIG. 4 illustrates cardiac signals which do not satisfy the sudden onset criterion of the invention.

FIG. 4 illustrates a high rate atrial event 23e and preceding events 23a–23d which do not satisfy the sudden onset criteria. Thus, as shown in FIG. 4, a high rate interval 28 is detected, but the previous two intervals are not sufficiently long to satisfy the predefined degree of interval change. Therefore, the high rate event 23e does not satisfy the sudden onset criteria defined with respect to FIGS. 2 and 3.

Figure 5:
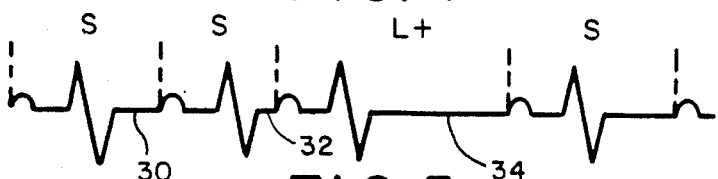
FIG. 5 illustrates other cardiac signals which do not satisfy the sudden onset criterion of the invention.

The sudden onset criteria is necessarily complex because it must differentiate a legitimate sudden onset high rate event from transitory events which occur relatively rapidly but which do not indicate a tachycardia. For example, a compensatory pause normally follows a premature cardiac contraction. This compensatory pause could appear to indicate a sudden onset of a reentrant tachycardia if the premature contraction occurs during a period of high rate atrial activity. With reference to FIG. 5, the pacemaker of the invention distinguishes this situation from an actual sudden onset tachycardia, because it finds that the two intervals 30 and 32 preceding such a pause 34, like those following it, are also shorter than the predefined high rate interval. This condition does not satisfy the sudden onset criterion, because the criterion requires that at least one of the intervals 30 and 32 exceed the predefined high rate interval. The pacemaker therefore correctly determines that a compensatory pause amid an ongoing high rate does not satisfy the sudden onset criterion for a reentrant tachycardia.

Figure 6:
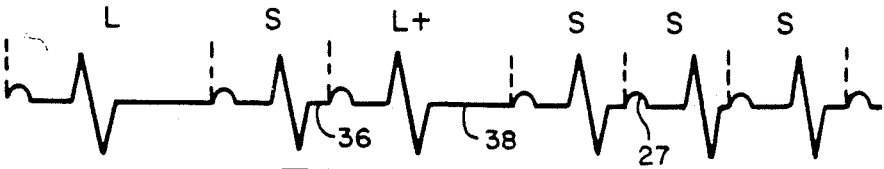
FIG. 6 illustrates another set of cardiac signals which satisfy the sudden onset criterion of the invention.

On the other hand, FIG. 6 illustrates a situation wherein the sudden onset criterion is satisfied in the presence of a high rate atrial event preceding a tachycardia event 27. In this case, it is assumed that a premature atrial contraction results in an interval 36 that is shorter than the programmed high rate interval, followed by an interval 38 that is longer than the programmed high rate interval. If the interval 38 is longer than the programmed high rate interval by at least the value of the defined degree of interval change, this combination satisfies the sudden onset criterion.

Thus, the sudden onset criterion of the pacemaker often is able to distinguish pace-terminable reentrant tachycardias from sinus tachycardia conditions which are not pace-terminable.

Atrial fibrillation or sinus tachycardia can have an onset which is as sudden as that of a pace-terminable tachycardia. Accordingly, it is desirable to provide additional means for distinguishing pace-terminable tachycardias. As mentioned above, it has been found that certain pace-terminable tachycardias are relatively stable in rate. On the contrary, non-pace-terminable tachycardias such as atrial fibrillation and sinus tachycardias resulting from exercise are generally not very stable. Rate stability is therefore a criterion which can be used to distinguish a pace-terminable tachycardia from fibrillation and exercise-related tachycardias. In the pacemaker of the invention, rate stability is programmed as a degree of interval change from 15 to 149 msec; and as a number of intervals from 8 to 250.

In operation, when the pacemaker detects three consecutive high rate intervals, it calculates an average interval length. The average interval length is determined by adding the value of the highest and lowest of the three detected interval values and dividing the sum by 2. Each subsequent consecutive high rate interval is then compared with this average. If subsequent consecutive high rate intervals do not vary by more than the programmed degree of interval change from the average, and this stability continues for the programmed number of intervals, the rate stability criterion is satisfied. If at any point a detected high rate interval varies from the average by more than the programmed degree of interval change, the count of stable events will be set to zero and the pacemaker will calculate a new average by using the current high rate interval and the two previous high rate intervals. Thereafter the pacemaker will again check for the predefined number of stable intervals. If at any time an interval greater than the predefined high rate interval is detected, the pacemaker will reset its stable rate counter to zero and will compute a new average when three successive high rate events are detected. It should generally be understood that the smaller the programmed degree of interval change and the greater the programmed number of intervals, the harder it is for the rate stability criterion to be satisfied.

The pacemaker is also capable of detecting a sustained high rate. This parameter is essentially a backup feature, with a programmable range that begins where the number of intervals for the high rate criterion stops. The sustained high rate criterion is therefore programmable from between 6 and 100 (always at least one more than the high rate criterion), up to 250 intervals. The sustained high rate criterion may be programmed only in conjunction with sudden onset and/or rate stability (i.e., combinations 3, 5, 7 and 9 listed above). If a tachycardia is detected and the high rate criterion is satisfied, but the selected sudden onset and/or rate stability criteria are not, satisfaction of the sustained high rate criterion will trigger the tachycardia pacing response. This operation generally insures that a pace-terminable tachycardia which continues for an extended period of time (the number of sustained high rate intervals) will be treated by the pacemaker, even if it does not exhibit sudden onset and/or rate stability.

The operation of the pacemaker with the above-identified criteria may be better understood with respect to an example using combination No. 9 with the following parameters:
High rate criterion is 399 msec for 12 intervals
Sudden onset degree of interval change is 256 msec
Rate stability criterion is 26 msec for a degree of interval change and 100 rate stable intervals
Sustained high rate criterion is 200 intervals at the defined high rate When the first high rate interval (i.e., the first interval measured as shorter than 399 msec) is detected, the pacemaker notes in memory that one short high rate interval has occurred. For each subsequent consecutive interval shorter than 399 msec, an additional entry is made. The high rate criterion is satisfied when 12 consecutive short intervals have been counted. If, before that point, an interval longer than 399 msec is measured, the high rate criterion is not satisfied. Counting begins anew with the next interval shorter than 399 msec.

Assessment of sudden onset begins immediately after sensing the first interval shorter than 399 msec. The pacemaker examines the immediately preceding interval. If it determines that this interval was 655 msec (399 plus the sudden onset degree of interval change of 256 msec) or more, it considers the initial requirement of the sudden onset criterion to be satisfied. It then examines the next preceding interval; if this interval was longer than 399 msec, the pacemaker considers the sudden onset criterion to be satisfied. If this interval is shorter than 399 msec, the pacemaker then looks at the next preceding interval. If that interval is longer than 399 msec, the criterion is satisfied.

Alternatively, if the interval immediately preceding the first high rate interval is longer than 399 msec but not longer by an amount at least equal to the sudden onset degree of interval change (i.e., it is shorter than 655 msec), the next preceding interval is examined. If this interval is longer than 399 msec by at least the sudden onset degree of interval change (the interval is 655 msec or longer), the sudden onset criterion is satisfied. Otherwise, a gradual onset tachycardia is diagnosed.

The pacemaker begins to assess rate stability simultaneously with the detection of a high rate event. If it finds three consecutive high rate intervals, for example 390, 350 and 360 msec, it averages the value of the longest of the three intervals (390 msec) with the value of the shortest (350 msec).

The average (370 msec) is then used as the basis for evaluating subsequent intervals. When 100 consecutive intervals that fall between 345 and 395 msec (i.e., not more than 26 msec variation from the average) have been counted, the rate stability criterion satisfied.

If, before 100 intervals have been counted, a high rate interval is measured that varies from the average by more than 26 msec, the counter is cleared. The pacemaker computes a new average using the current high rate interval and the two preceding it. The pacemaker then continues to assess following high rate intervals with respect to the newly computed average.

The sustained high rate counter operates in the same manner as the high rate counter. Sensing of the first interval shorter than 399 msec is registered by both counters. Both then count each consecutive interval of less than 399 msec. The high rate counter stops when 12 intervals have been counted. However, the sustained high rate counter will continue to count intervals until it reaches 200, which satisfies the sustained high rate criterion (like the high rate counter, it is cleared if an interval longer than 399 msec is measured before its programmed number of intervals have been counted). In the event that the criterion or criteria with which sustained high rate was programmed are not satisfied, the pacemaker uses the sustained high rate criterion by itself to identify a tachycardia which should be treated.

If all the requirements of programmed tachycardia recognition modes are met, the pacemaker enters a diagnosis of pace-terminable tachycardia. Thus, in the example, a pace-terminable tachycardia is diagnosed if the selected criteria of combination No. 9 is satisfied.

When the pacemaker of the invention, detects a pace-terminable tachycardia, it attempts to break the cycle of the tachycardia by applying stimulus pulses to the atrium. The basic therapeutic modality of the pacemaker is a burst which for the purpose of the following discussion is defined as one or more electrical stimulating pulses applied to the heart and timed to interrupt the tachycardia. The treatment modality of the pacemaker is programmed with respect to three variables. The first of these is the number of pulses from 1 to 250 in a treatment burst. The second variable is the length of a delay interval which is timed between a sensed synchronizing tachycardia event and the first pulse of the burst. This interval may be programmed from 3 to 653 msec in 2.56 msec steps. The third variable is the burst cycle length which is the pulse-to-pulse interval within a burst. The burst cycle length may be programmed from 10 to 653 msec in 2.56 msec steps.

The initial value of the delay and/or the burst cycle length of the pacemaker may be programmed by fixed or adaptive. In the fixed mode, the delay and burst cycle length are programmed as fixed values in milliseconds. In the adaptive mode, the delay and/or burst cycle length are programmed as a percentage of the interval of the detected tachycardia. In the adaptive mode, the timing of the treatment modality therefore depends upon the rate of the detected tachycardia. As an example, the delay and burst cycle lengths may be programmed as seventy-five percent of the detected tachycardia interval. This provides some adaptability in treating tachycardias which exhibit rate variations over time.

The value of the delay or burst cycle length may be changed in a "scanning" mode wherein the values are incremented or decremented over successive bursts. In the scanning mode, the value of the burst cycle length or the delay is changed in one of three sequences: incremental, decremental, or a search pattern which is alternately incremented and decremented. A scanning burst generally increases the effectiveness of the pacemaker's attempts to locate a characteristic "termination zone" for the tachycardia. If a stimulus is provided in the appropriate termination zone, the tachycardia will be interrupted. In the scanning mode, an initial value of the burst cycle length or delay is thus incremented, decremented or alternately incremented and decremented in a search pattern in an effort to apply a stimulus within the termination zone. A scanning burst sequence may be programmed with either fixed or adaptive initial intervals for burst cycle length or delay. Thus, the initial burst cycle length or delay in a scanning mode may be programmed to a fixed value or may be computed as a percentage of the rate interval of the detected tachycardia.

The burst scanning mode is programmed with respect to three parameters: step size, number of steps and number of sequences. The step size for a scanning sequence is the amount by which the burst cycle length or delay are increased or decreased for each successive burst. The pacemaker of the invention may be programmed to a step size of, for example, from 2.56 to 38.4 msec. As an example, if a burst is programmed to seven pulses, with a delay of 200 msec and an initial burst cycle length of 251 msec, scanning the burst cycle length incrementally with a step size of 10.2 msec will cause the pulses of the second burst to a have a cycle length of about 261 msec, the pulses of the third burst to have a cycle length of 271 msec, and so on.

On the other hand, if scanning is programmed to the alternately incremental/decremental sequence, a further programmable option allows the decremental step to be programmed to one-half the step size of the increment instead of to the same millisecond value as the increment. For example, a burst cycle length initially programmed to 251 msec with incremental/decremental scanning steps programmed to 10.2 msec and one-half step size (i.e. 5.1 msec) respectively, will initially be incremented from 251 to about 261 (251 +10) and will thereafter be decremented from 261 to 246 (251 −5). Thereafter the step size will be again incremented to 271 and then decremented to 241 and incremented again to 282 msec, and so on. The increment/decrement sequence will be carried out for the predefined number of steps for the scan. The number of steps is a scanning variable that defines the number of times that the burst cycle length or the delay will be increased or decreased by the predetermined step size. The number of steps is programmable from 2 to 31.

The final scanning variable is the number of sequences. This is the number of times a scan sequence of, for example from 2 to 31 steps, is to be repeated. The number of sequences is programmable from 1 to 8. Thus, a predefined scan sequence can be repeated for up to eight times in an effort to locate the termination zone of a tachycardia and thus terminate the tachycardia.

The physician may supplement or fine tune a basic therapeutic pacing modality by resetting a scanning sequence if the rate of the tachycardia changes during the scanning sequence outside an acceptable rate of change. In programming this reset feature, the physician selects a millisecond value for a "difference interval". The scanning sequence will be reset to its initial values if the difference between the rate interval of the originally-detected tachycardia which initiated the scan and the rate interval of the presently detected tachycardia during the scan exceeds this selected difference interval. That is, the scanning sequence will be reset if the interval of the tachycardia detected within the scan is either shorter or longer than the tachycardia interval which initiated the scan, by more than the difference interval. It should be appreciated that the reset option is provided to reset a scanning sequence to its beginning point when there is a large change in tachycardia rate, because resetting the scan will increase the probability that the scan will converge on the termination zone of the "new" tachycardia. This resetting of the scan sequence should be more efficacious in terminating a tachycardia where the scanned interval is adaptively defined.

If a tachycardia has been successfully terminated by a scanning burst, a "use memory" function of the pacemaker may be selected to permit immediate reimplementation of the successful burst parameters when a following similar tachycardia is detected. When the use memory function is selected in conjunction with a scanning sequence, the pacemaker remembers the intervals of delay and burst cycle length which were used to successfully terminate a tachycardia. When the next tachycardia is detected, the pacemaker begins with the remembered successful values of delay and burst cycle length. This increases the probability that a minimum number of bursts will be used to terminate the new tachycardia. If the remembered parameters do not succeed, the pacemaker then scans in an alternating increment/decrement sequence. If this increment/decrement sequence terminates the tachycardia, the new successful values of delay and burst cycle length are stored in memory. If the increment/decrement sequence fails, the pacemaker will then deliver the full number of burst scan sequences beginning at the programmed values.

The selected use memory function may be restricted by electing a related "need interval similarity" function which restricts the use memory function to tachycardias having an interval similar to that of the last successfully terminated tachycardia. In operation, a difference interval is selected with the programming of the need interval similarity feature to define an interval range within which tachycardias will be deemed similar. The interval of a newly-detected tachycardia may not vary by more then this difference interval from that of the last successfully terminated tachycardia to qualify as a similar tachycardia. The difference interval may be programmed with values of from 15 to 149 msec in 10 msec steps.

It should be noted that if the use memory function is selected and the pacemaker applies a burst scan with an alternating increment/decrement sequence, it is possible that part of the sequence will fall outside of the pacemaker's operational range of from 0 to 653 msec. If this occurs, scanning simply stops when the limit is reached (i.e., incremental: 653 msec; decremental: 0 (for delay) or minimum cycle length (for burst cycle length). With a search pattern, scanning may stop in one direction and continue in the other. The pacemaker will count attempts to pace in the direction in which it is beyond range as well as outputs in the direction in which it is still within range, until the programmed number of steps have been counted.

If an antitachycardia treatment burst is not scanned, it may be programmed in the autodecremental mode. In the autodecremental mode a burst is programmed so that the cycle length (the pulse-to-pulse interval) within the burst will automatically decrement from an initial value by a programmable amount from 2.56 to 38.4 msec. In other words, the interval of the pulses within a burst can be automatically decremented from one pulse to the next. A minimum cycle length variable is defined to limit the interval to which pulses can be decremented within a burst.

The number of attempts for any non-scanned burst is programmable from 1 to 31. If a tachycardia is detected, the pacemaker will apply the selected number of bursts in an effort to terminate the tachycardia. If scanning is programmed, the selected number of sequences determines the number of times that the scanning burst is repeated.

Antitachycardia burst treatments, including any programmed scanning sequence, will cease when a tachycardia is terminated. The pacemaker determines whether a tachycardia has been terminated by monitoring the rate of atrial events between bursts. The pacemaker checks only the atrial rate when it is reattempting to treat a tachycardia, other criteria which were employed to initiate the treatment of the tachycardia are not rechecked. Thus, when a pace-terminable tachycardia is detected, the pacemaker will apply a burst in a predefined treatment modality and will thereafter check the rate of atrial events. If the pacemaker detects the lesser of the programmed number of high rate intervals or fifteen such intervals, it will again attempt to terminate the tachycardia. If the atrium reverts to a sinus rate lower than the tachycardia rate prior to detecting the required number of consecutive high rate intervals, the pacemaker will record a successful treatment of the tachycardia and will return to its bradycardia mode.

The pacemaker of the invention may be programmed to define a primary treatment modality and a secondary treatment modality for terminating tachycardias. Each of the modalities may define a different selected burst sequence for terminating a tachycardia. In operation, if a tachycardia is detected, the primary modality will initially be applied to terminate the tachycardia. If the primary modality fails after the programmed number of attempts (or number of sequences if the burst scanning mode is programmed), the pacemaker will attempt the secondary treatment modality for its programmed number of attempts or sequences.

If the programmed primary and secondary pacing modalities both fail to interrupt a tachycardia, the physician must decide ahead of time whether further attempts should be made and, if so, under what conditions. In view of the fact that burst pacing has been found to be effective, a failure of primary and secondary burst pacing treatments might reasonably suggest that the unresponsive tachycardia is sinus or non-pace-terminable in origin. The most conservative course of treatment would therefore be to suspend burst responses in order to avoid pacing into a sinus rhythm. This conservative treatment mode would be achieved by selecting the "no restart" option. However, if a physician judges that it will be necessary to continue to attempt to terminate a tachycardia after the failure of primary and secondary modes of treatment, he may select one of the following four options to restart treatment:

1. Restart if the high rate criterion is reestablished;
2. Restart if the rate stability criterion is established in addition to the high rate criterion;
3. Restart if a sustained high rate criterion is reestablished; and
4. Restart if either rate stability or sustained high rate is reestablished.

The order of application of the primary and secondary treatment modalities may be changed in response to information regarding a prior successful treatment of a tachycardia. Thus, if the "can use secondary modality first" feature of the pacemaker is selected, the secondary treatment modality will be applied prior to the primary treatment modality whenever an immediately preceding tachycardia was terminated with a history indicating that the primary modality failed and the second modality was successful in treating the tachycardia. In operation, when the "can use secondary modality first" feature is elected, the pacemaker automatically implements the secondary modality first when it detects a tachycardia condition with a rate that is "similar" to the rate of a previous tachycardia which was successfully treated by only the secondary modality. If the initial attempt to terminate the tachycardia by the secondary modality fails, the primary modality will be attempted. If the primary modality also fails, further attempts will depend upon which of the restart options has been selected. If restart is selected and satisfied, attempts will continue in the order: primary, secondary, primary, secondary for as long as the high rat criterion is detected.

When the "can use secondary modality first" feature is programmed, a value for the "interval difference" must also be selected to determine a range within which a detected tachycardia will be deemed similar to a previously successfully treated tachycardia. Thus, the pacemaker will use the second modality first only for tachycardias whose rates do not vary by more than the selected interval difference from the previously successfully terminated tachycardia.

The pacemaker of the invention utilizes a series of diagnostic data counters in which it accumulates and stores basic ECG data, including the following events:
1. Number of times high rate criterion met;
2. Number of times sudden onset criterion met;
3. Number of times rate stability criterion met;
4. Number of times sustained high rate criterion met;
5. Number of times primary modality used;
6. Number of times secondary modality used;
7. Number of times secondary modality used first;
8. Most recent primary burst parameters (tachycardia interval, burst cycle length and delay);
9. Most recent secondary burst parameters (tachycardia interval, burst cycle length and delay).

The diagnostic data counters are reset automatically whenever the physician changes the pacemaker's operating mode or tachycardia detection/response parameters.

A minimum burst cycle length is programmed into the pacemaker of the invention in order to insure that the rate of burst pulses applied to the atrium will not exceed a predefined value, reducing the likelihood of hazardous effects. When the burst cycle length is programmed to a percentage of the tachycardia rate or when the burst is programmed in the autodecremental mode, the minimum cycle length parameter is programmed to provide a maximum burst rate (i.e. a minimum burst cycle length) which will not be exceeded by the pacemaker. Thus, in burst modalities herein the rate of burst pulses is automatically increased by the pacemaker, the pacemaker is controlled to insure that bursts having an undesirably high rate are not applied to the atrium.

The above-described tachycardia detection and treatment functions are implemented in the pacemaker of the invention by a computer program which controls the operation of the microprocessor and associated memory devices to achieve the indicated operations. The computer code for the microprocessor is described in the Program Listing is the microfiche appendix pursuant to 37 CFR 1.96 The Program Listing is not provided in the actual assembly language which is required to operate the microprocessor of the preferred embodiment of the invention. In order to facilitate, an understanding of the invention, the Program Listing instead documents and explains the steps of the computer program which operates the microprocessor to achieve the described functions of the invention.

The computer system for the microprocessor will hereafter be generally described with reference to the descriptive program listing and FIG. 7, which illustrates a block diagram of the functional operation of the pacemaker of the invention.

Figure 7:
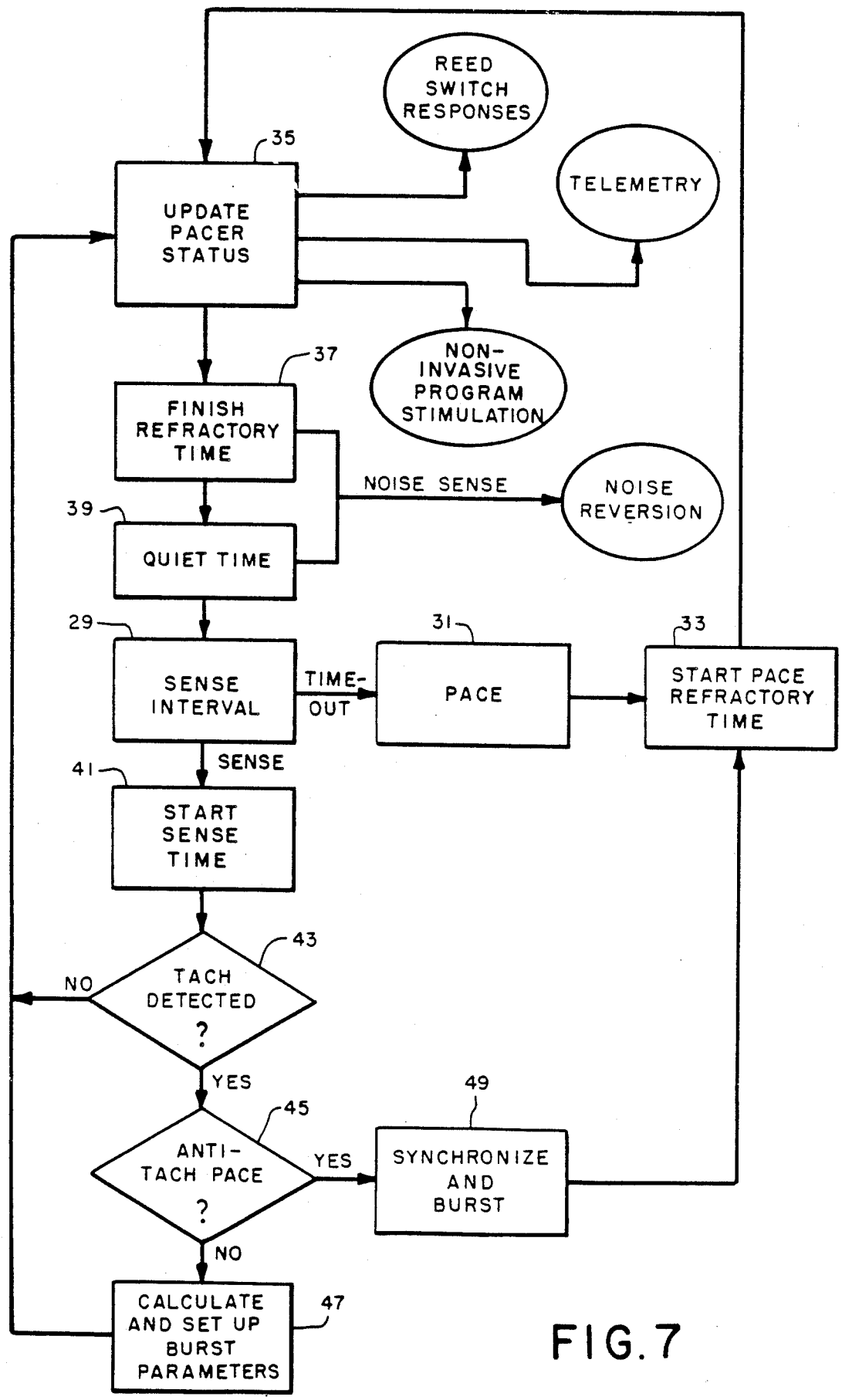
FIG. 7 illustrates a block diagram of the functional operation of the pacemaker of the invention.

With reference to FIG. 7, in bradycardia operation the pacemaker senses atrial events during a sense interval 29. If no event is detected within a predefined timed interval (timeout), the atrium is paced at 31 and a refractory interval is started at 33. Thereafter, program control is passed to an update pacer status routine 35 (see page 17 of program listing) which determines if newly programmed variables have been applied to the pacemaker. If so, the pacemaker stores the newly programmed variables and clears all status flags and diagnostic counters so that the pacemaker can begin carrying out its new instructions. If new programmed variables have not been provided, the update pacer status routine continues with a series of status checks and transfers program control in accordance with the operational status of the pacemaker. Thus, the update pacer status routine will respond to activation of the reed switch 16 (FIG. 1), a request for transmission of telemetry or a request for initiation of noninvasive program stimulation when it is desired to evaluate parameters for tachycardia pacing. If the status checks do not initiate a transfer of program control, the pacemaker completes its refractory time at 37 and begins timing a "quiet time" interval at 39. If noise signals are detected during timing of the refractory time or the quiet time, program control will be transferred to a noise reversion routine and eventually control will be returned to update pacer status at 35. If noise is not detected, the pacemaker will again begin sensing atrial events at 29.

If a sense event is detected, the pacemaker will start a sense refractory interval at 41 and will thereafter check the tachycardia detection criteria at 43 to determine if a pace-terminable tachycardia has occurred. If a pace-terminable tachycardia is not detected, control is returned to the update pacer status routine at 35. If a pace-terminable tachycardia is detected, the program determines at 45 if an antitachycardia burst should be generated during the present cycle. If burst parameters have not been calculated, program control is transferred from 45 to calculate the burst parameters at 47 and the program then returns to update pacer status at 35. The program thereafter detects a sense event at 29, starts timing a sense refractory interval at 41, verifies that a pace-terminable tachycardia has been detected at 43 and determines that a burst must be generated at 45. Thereafter, a synchronized burst is generated at 49, a pace refractory interval is started at 33 and program control is returned to update pacer status at 35.

With reference to the listing, the described update routine is shown at page 17 and the described "quiet time" routine is shown at page 13. The sense interval function 29 of FIG. 7 is generally shown following the label "sense-time" at page 14. The label "start-up" at page 15 generally designates the program entry point when a sense event is detected and a refractory interval must be timed, for example as illustrated at 41 of FIG. 7.

After starting the refractory timed interval, the rate interval for the event is known. Accordingly, program control moves to the point 43 of FIG. 7 to determine if a tachycardia has occurred. The detection of the tachycardia is carried out in the "Check-for-Tach" routine of page 20 of the listing. In this routine the reed switch 16 is initially interrogated to determine if the switch has been selected to provide an antitachycardia burst regardless of the detected rate. If the switch has been activated for this purpose, program control is transferred to a point which will initiate the delivery of a burst. If the reed switch is not activated, the program determines if the most recent interval is less than the defined tachycardia rate limit interval. That is, the program determines if the most recent interval is an "S" interval which is shorter than the defined tachycardia rate interval. If a tachycardia interval is detected, program control is transferred to a "TACHY1" routine at page 21. Alternatively, if a tachycardia event is not detected, the program determines if a tachycardia therapy is not in progress, a tachycardia condition is not detected, or if this is not the first detected interval after a burst. If any of these conditions are true, counters which accumulate counts for the detection of a tachycardia are cleared and program control is transferred to the update routine. In other words, the program has detected a non-tachycardia interval and therefore will begin counting from a zero count if a tachycardia interval is subsequently detected. On the other hand, if antitachycardia therapy is in progress, a tachycardia condition is detected, or the detected atrial event is the first interval after a burst, a high rate count which counts the number of tachycardia events is incremented. This is done in the case of the first atrial event following a burst, because such an event is assumed to be a high rate interval. Following the incrementing of the high rate count, program control is transferred to the update routine.

With reference to FIG. 7, if a high rate tachycardia event is detected at 43 and all programmed high rate criteria are met, burst parameters are set at 47 and program control is returned to the update routine at 35. Thereafter, on the next atrial event, a burst is generated at 49 to attempt to treat the detected tachycardia. Therefore the atrial event which satisfies the tachycardia detection criteria does not synchronize the generation of a burst. Instead, the atrial event following the detection of a tachycardia synchronizes the burst. After the burst a refractory interval is timed at 33 and program control is then passed to the update routine at 35.

As discussed above, the "TACHY1" routine at page 21 operates in response to the detection of a high rate atrial event. When such an event is detected, the routine initially interrogates the status of the reed switch and, if the reed switch is set, responds in the appropriate programmed manner. If the reed switch is not set, the program then determines if noise has been detected. If noise was detected, the program transfers control to the update routine. If noise was not detected, the program determines if a pace-terminable tachycardia has already been detected. If it has, a burst is then generated, synchronized with the following atrial event, as discussed above.

If a pace-terminable tachycardia has not already been detected, the program determines if the stable rate criterion has been satisfied. If this criterion has been satisfied, the program skips around and therefore avoids the stable rate criterion test. If the stable rate criterion has not previously been satisfied, the program determines if the sense event is stable, that is if the period of the detected high rate event differs from a computed average by less than a predefined maximum interval. Thus, the detected sense event is determined to be unstable if the absolute value of the difference between the computed average and the current interval is greater than the predefined difference interval.

If the sense event is unstable, a new average is computed by calling a "find extremes" routine at page 42 which examines the present and two preceding intervals and generates the average of the sum of the maximum and minimum of these intervals. On the other hand, if the sense event is stable, a rate stability counter is incremented and the counter is then checked to determine if a predefined number of successive high rate atrial events have occurred at the stable rate. If the predefined number of events have occurred at the stable rate, a stable rate detected flag is set to indicate that the stable rate criterion has been met. After the stable rate flag is set or if it is determined that the preselected stable rate count has not yet been reached, the program determines if the preselected high rate criterion has been satisfied. If the high rate criterion has not been satisfied, the high rate counter is incremented and program control is passed to the program steps of page 21 to determine if the sudden onset criterion is met. If the high rate criterion was detected, the program skips over the sudden onset test and goes to the "TACHY2" program routine at page 24 to check the program requirements for deducing a reentrant tachycardia against the presently determined conditions.

If, as discussed above, the high rate criterion has not been detected and the high rate count has been incremented, the program at page 23 determines if the sudden onset criterion is met. In operation, the program determines if therapy is not in progress and if the high rate count equals one. If either of these conditions are false, it is unnecessary to test the sudden onset criterion. Accordingly, the program branches to the "TRIG1" routine at page 24 which checks if there have been enough fast beats to consider the detected rhythm a tachycardia. On the other hand, if the conditions are false, the program next determines if the third most recent interval was a relatively short "S" interval which meets the defined criterion for a high rate tachycardia event. If the third most recent interval was not a high rate interval (e.g., it was not an S) the program next determines if the difference between this third most recent interval and the most recent interval is greater than the variable "ONSET" which is part of the predefined sudden onset criterion. If the difference of the indicated intervals is greater than ONSET, the sudden onset detected flag is set true to indicate that the sudden onset criterion has been met. However, if the difference between the intervals is less than the value of ONSET, the sudden onset detected flag is set false to indicate that the sudden onset criterion has not been met.

If the third most recent interval was a high rate atrial event, the fourth most recent interval is checked to determine if it exceeds the defined high rate interval (i.e., is at "L"). If the fourth most recent interval was not a long interval (i.e., it was a high rate event), then the sudden onset flag is set false. However, if the fourth most recent interval was a long interval, the program determines if the difference between the second most recent interval and the most recent interval is greater than the value of ONSET. That is, the program determines if the second most recent interval is greater than the most recent interval by at least the amount of ONSET. If the difference between the intervals is greater than ONSET, the sudden onset detected flag is set to indicate that the sudden onset criterion has been met. However, if the difference of the intervals is less than ONSET, the sudden onset detected flag is set false to indicate that the criterion has not been met. After the sudden onset testing has been completed, the program transfers control to the TRIG1 routine of page 24 which checks to see if there have been enough fast beats to consider the atrial rhythm a tachycardia.

In the TRIG1 program routine, the program initially determines if the high rate count equals the preselected required high rate count which defines the high rate criterion. If the required number of counts has been reached to satisfy the high rate criterion, the high rate detected flag is set true. Program control is then passed to the TACHY2 routine of page 25 which checks the programmed requirements for deducing a pace-terminable tachycardia against the requirements which have been measured.

If in the TRIG1 routine the high rate criterion has not been met, the program next determines if therapy is in progress and if the high rate count equals the lower of two predetermined numbers, HIGH RATE COUNT or 15. If these conditions have not been satisfied, program control is passed to the UPDATE routine previously described at page 16. If these conditions are true, it is known that a tachycardia condition has been previously detected and the program is now checking to see if the condition still exists after treatment has been applied. The program will therefore set the high rate detected flag true, because the HIGH RATE COUNT number or 15 high rate events have been detected after the attempt to treat the tachycardia. Also, the tachycardia detected flag is set true to indicate that a tachycardia has been detected following treatment. Program control is then passed to the antitachycardia therapy routine starting at page 28.

As previously discussed, the TACHY2 routine is entered after the high rate detected flag has been set in TRIG1. In TACHY2, the program first determines if a sustained high rate flag is clear. This flag will be set if the above-described sustained high rate criterion has been met. If the sustained high rate flag is clear, the high rate counter is incremented and the program then determines if the high rate count equals the required count for satisfying the sustained high rate criterion. If the sustained high rate criterion is satisfied, the sustained high rate detected flag is set true.

If the sustained high rate flag was not clear or the high rate count was not equal to the required count for sustained high rate, the program checks to determine if the preselected tachycardia criteria have been met. If the criteria have been met, program control is transferred to the antitachycardia therapy routine starting at page 28 to set up the "burst" treatment in the predetermined modality. If the tachycardia criteria have not been met, the program checks to determine if the primary and secondary therapies have failed. If these therapies have not failed, the program next determines if the detected conditions meet the composite tachycardia detection criteria. If they do meet these criteria, the tachycardia detected flag is set and the tachycardia is treated.

If the primary and secondary therapies failed, the program determines if the restart option has been selected. If this option has not been selected, program control is transferred to UPDATE. However, if the restart option has been selected, the program determines if the detected conditions meet the predefined composite restart detection criteria. If they do not, program control is passed to UPDATE. On the other hand, if the composite restart detection criteria are satisfied, the tachycardia detected flag is set and the tachycardia is treated.

The antitachycardia therapy routine of page 25 is entered after a pace-terminable tachycardia is initially diagnosed or is re-diagnosed in the case of an ineffective burst. The antitachycardia therapy routine and the burst delay calculations routine prepare the pacemaker for producing a burst in accordance with the preselected treatment modality. As previously discussed, the burst is synchronized with respect to the sense event which follows the event at which the pacer-terminable tachycardia is detected.

The antitachycardia therapy routine keeps various flags, for example Burst, Primary Therapy, Secondary Therapy and Both Therapies Failed up-to-date. The routine also clears other flags such as Rate Stability and Persistent High Rate if required and loads the Attempt Counter with either a preselected primary attempt limit or secondary attempt limit to define the number of attempts in the primary and secondary treatment modalities which will be carried out before the restart instruction is checked. The routine further decrements and checks the status of the attempt counts to determine whether the treatment therapy should be changed. The routine also determines if the secondary therapy may be performed first. If the secondary therapy can be performed first, the program applies the secondary therapy first if the present tachycardia rate is similar to the rate of the last tachycardia which was successfully treated by the secondary mode of treatment and is either not similar to the last primary treated tachycardia or, if it is similar, the previous similar tachycardia was not successfully treated by the primary therapy.

The routine of pages 31 and 32 makes the required calculations for setting up a burst treatment in the required treatment modality. This portion of the program computes S1, the delay from the sense event to the first treatment pulse and S2, the pulse-to-pulse interval in a burst. These values are determined in accordance with selected fixed delay values or delay values derived by adaptive calculations. A Swap flag is utilized to operate the code in the computational manner required for the primary or secondary therapies.

The CALC1 program routine of page 33 performs the necessary calculations for setting up the parameters for all scanning therapies. Again, the Swap flag, which is set in the burst delay calculations, is used to operate the code to define the parameters for primary and secondary therapies.

The DELIVER BURST routine at page 35 is employed to deliver a burst treatment for a detected pacer-terminable tachycardia. This routine applies the required number of pulses in a defined burst and compares the defined pulse-to-pulse burst interval with a selected minimum burst delay. If the defined burst interval is less than the value of the minimum burst delay, the burst interval is set equal to the value of the minimum burst delay to avoid excessively rapid stimulation of the heart when treating the tachycardia.

The remaining program routines of pages 37–46 provide additional features and perform routine program control functions for the pacemaker of the invention. Thus, the TELEM routine of page 37 is utilized to perform all telemetry functions for the pacemaker. The Electro-Physiology Study routine of page 39 is employed to set-up the delay and cycle length for the first part of an electrophysiological burst. The EPXTRA routine adds extra stimuli at the end of a burst, if required. The PACE routine of page 40 operates to deliver the required pacing signals for the pacemaker. The subroutine CLEAR of page 41 operates to set initial values for state flags and certain variables of the program. The subroutine FIND-EXTREMES of page 42 calculates the interval average which is required to determine the stable rate criterion. The subroutine HR-OVERRIDE at page 43 activates a high rate override feature of a linear integrated circuit of the pacemaker. The subroutine UPDATE LINEAR IC at page 44 updates the linear IC as required. The Shift-Intervals subroutine of page 45 stores the most recent rate interval and associated three preceding rate intervals and updates the intervals by shifting as required. Finally, the SLEEP routine of page 46 allows the microprocessor to operate in a quiescent or sleep state while timing burst delays.

Although a program and particular ranges of parameter values for detecting and treating pace-terminable tachycardias have been particularly described, it should be understood that other programs and parameter values can be employed to implement the desired detection and treatment criteria, without departing from the invention. It should therefore be understood that the invention may be embodied in other specific forms without departing from its spirit or essential characteristics. The present embodiment is, therefore, to be considered in all respects as illustrative and not restrictive. The scope of the invention is indicated by the claims rather than by the foregoing description. All changes which come within the meaning and range of the equivalents of the claims are, therefore, intended to be embraced therein.

We claim:

1. An antitachycardia pacemaker, comprising:
   means for detecting electrical cardiac events occurring in at least one chamber of the heart;
   means for detecting said events which exceed a selected tachycardia rate;
   means for determining the relative rate stability of the events which exceed said tachycardia rate;
   means responsive to said event detecting means and said stability determining means for detecting a pace-terminable tachycardia when at least a first selected number of said events exceed said tachycardia rate and a second selected number of said events have a defined rate stability; and
   means responsive to said pace terminable tachycardia detecting means for pacing the heart to terminate the tachycardia.

2. The antitachycardia pacemaker of claim 1, wherein said means for pacing includes:
   means for generating electrical signals according to either a primary tachycardia treatment modality comprising a first set of electrical signals and a sequence for altering selected characteristics of said first set of electrical signals or a secondary tachycardia treatment modality comprising a second set of electrical signals and a second sequence for altering selected characteristics of said second set of electrical signals; and
   means for applying the primary and secondary treatment modalities to interrupt a detected pace-terminable tachycardia in a selected order of preference.

3. The antitachycardia pacemaker of claim 2, wherein said means for applying the primary and secondary treatment modalities includes means for applying the primary modality before the secondary modality to interrupt a currently detected pace-terminable tachycardia, unless the secondary modality was the only modality which successfully treated a previous similar detected pace-terminable tachycardia, in which case the secondary modality is applied before the primary modality.

4. The antitachycardia pacemaker of claim 2, further including means for selectively retrying the primary treatment modality a first selected number of times if it fails to terminate the tachycardia and thereafter selectively retrying the secondary treatment modality a second selected number of times if it fails to terminate the tachycardia.

5. The antitachycardia pacemaker of claim 4, including means for restarting the primary and secondary treatment modalities if a tachycardia is unsuccessfully treated and selected restart conditions are met by the continuing tachycardia.

6. The antitachycardia pacemaker of claim 5, including means for restarting treatment by the primary and secondary modalities if the rate of said continuing tachycardia exceeds said tachycardia rate for a selected high rate number of events.

7. The antitachycardia pacemaker of claim 5, including means for restarting treatment by the primary and secondary modalities if the rate of said continuing tachycardia exceeds said tachycardia rate for a selected high rate number of events detected by both the tachycardia rate detecting means and the relative rate stability detecting means.

8. The antitachycardia pacemaker of claim 5, including means for restarting treatment by said primary and secondary modalities if the rate of said continuing tachycardia exceeds said tachycardia rate for a selected sustained high rate number of events which exceeds the counted high rate number of events that resulted in tachycardia detection.

9. The antitachycardia pacemaker of claim 5, including means for restarting treatment by said primary and secondary modalities if the rate of said continuing tachycardia exceeds said tachycardia rate for a selected high rate number of events detected by said relative rate stability detecting means or the rate of said continuing tachycardia exceeds said tachycardia rate for a selected sustained high rate number of events which exceeds said high rate number of events.

10. The antitachycardia pacemaker of claim 1, wherein said means for pacing includes means for selectively applying at least one burst of electrical signals to terminate a detected pace-terminable tachycardia, the burst starting a selected start delay time following a detected synchronizing event and including a selected number of electrical pulses, successive pulses being separated by a selected burst cycle interval.

11. The antitachycardia pacemaker of claim 10, further including means for remembering the values of the start delay time, number of burst pulses and burst cycle interval for a successfully terminated tachycardia and for selectively applying these values to terminate a subsequent similar detected pace-terminable tachycardia.

12. The antitachycardia pacemaker of claim 11, further including means for defining said subsequent similar tachycardia having a rate within a selected range of the rate of the previously successfully terminated tachycardia.

13. The antitachycardia pacemaker of claim 10, further including means for defining fixed values for said start delay time and burst cycle interval.

14. The antitachycardia pacemaker of claim 10, further including means for defining adaptive values for said start delay time and burst cycle interval, each adaptive value being defined as a selected percentage of the rate interval for the associated detected pace-terminable tachycardia.

15. The antitachycardia pacemaker of claim 14, further including means for selecting a minimum value for said burst cycle interval and for preventing burst pulses from being generated with cycle intervals less than said minimum value.

16. The antitachycardia pacemaker of claim 15, further including means for generating burst pulses having said minimum value burst cycle interval in response to the definition of adaptive values of burst cycle intervals less than said minimum value.

17. The antitachycardia pacemaker of claim 10, further including means for selectively incrementally scanning the initial values of said start delay time and burst cycle interval by selected increments for a selected number of steps from burst to burst.

18. The antitachycardia pacemaker of claim 10, further including means for selectively decrementally scanning the initial values of said start delay time and burst cycle interval by selected decrements for a selected number of steps from burst to burst.

19. The antitachycardia pacemaker of claim 10, further including means for selectively and alternately incrementing and decrementing the initial values of said start delay time and burst cycle interval by selected increments and decrements for a selected number of steps from burst to burst.

20. The antitachycardia pacemaker of claim 19, further including means for defining said selected decrement as a fraction of said selected increment.

21. The antitachycardia pacemaker of claim 19, further including means for defining said selected decrement as onehalf of said selected increment.

22. The antitachycardia pacemaker of claim 10, further including means for selectively and automatically decrementing said initial value of said burst cycle interval within a burst by a selected amount for providing decreasing interval burst pulses within the burst.

23. The antitachycardia pacemaker of claim 22, further including means for selecting a minimum value for said burst cycle interval and for preventing burst pulses from being generated with cycle intervals less than said minimum value.

24. The antitachycardia pacemaker of claim 22, further including means for generating burst pulses having said minimum value burst cycle interval in response to the definition of decremental values of burst cycle intervals less than said minimum value.

25. The antitachycardia pacemaker of claim 1, further including means for determining a relative suddenness of onset comprising a rate of change of the rate of events which exceed said selected tachycardia rate, and wherein said means for detecting a pace-terminable tachycardia comprises means for detecting a pace-terminable tachycardia when a selected high rate number of said events exceed said tachycardia rate, said selected number of said events have said rate stability and said events have an onset which exceeds a selected rate of onset.

26. The antitachycardia pacemaker of claim 1, further including means for determining a relative suddenness of onset comprising a rate of change of the rate of events which exceed said selected tachycardia rate, and wherein said means for detecting a pace-terminable tachycardia comprises means for detecting a pace-terminable tachycardia when a selected high rate number of said events exceed said tachycardia rate and said selected number of said events have said defined rate stability or said events have an onset which exceeds a selected rate of onset.

27. The antitachycardia pacemaker of claims 25 and 26, further including means for detecting a pace-terminable tachycardia when a selected sustained high rate number of said events exceed said tachycardia rate, said sustained high rate number being greater than said selected high rate number.

28. An antitachycardia pacemaker selected treatment modalities to terminate the tachycardia, said pacemaker comprising,
   means for detecting electrical cardiac events occurring in at least one chamber of the heart;
   means for detecting said electrical cardiac events which exceed a selected tachycardia rate;
   means for determining a relative suddenness of onset comprising a rate of change of rate of said electrical cardiac events;
   means responsive to said event detecting means and said relative suddenness of onset determining means for detecting a pace-terminable tachycardia when a first selected number of said cardiac events exceed said tachycardia rate and said events have an onset which satisfies a sudden onset criterion; and
   means responsive to said pace-terminable tachycardia detecting means for pacing the heart to terminate the tachycardia.

29. The antitachycardia pacemaker of claim 28 wherein said heart pacing means further comprises:
   means for generating electrical signals according to either a primary tachycardia treatment modality comprising a first set of electrical signals and a sequence for altering selected characteristics of said first set of electrical signals or a secondary tachycardia treatment modality comprising a second set of electrical signals and a second sequence for altering selected characteristics of said second set of electrical signals; and
   means for applying the primary and secondary treatment modalities to the heart to interrupt a detected pace-terminable tachycardia in a selected order of preference.

30. The antitachycardia pacemaker of claim 29, wherein said means for applying the primary and secondary treatment modalities includes means for applying the primary modality before the secondary modality to interrupt a currently detected pace-terminable tachycardia, unless the secondary modality was the only modality which successfully treated a previous similar detected pace-terminable tachycardia, in which case the secondary modality is applied before the primary modality.

31. The antitachycardia pacemaker of claim 29, further including means for selectively retrying the primary treatment modality a first selected number of times if it fails to terminate the tachycardia and thereafter selectively retrying the secondary treatment modality a second selected number of times if it fails to terminate the tachycardia.

32. The antitachycardia pacemaker of claim 31, including means for restarting the primary and secondary treatment modalities if a tachycardia is unsuccessfully treated and selected restart criteria are met by the continuing tachycardia.

33. The antitachycardia pacemaker of claim 32, including means for restarting treatment by the primary and secondary modalities if the rate of said continuing tachycardia exceeds said selected tachycardia rate for said selected high rate number of events.

34. The antitachycardia pacemaker of claim 32, including means for restarting treatment by said primary and secondary modalities if the rate of said continuing tachycardia exceeds said selected tachycardia rate for a selected sustained high rate number of events which exceeds said selected high rate number of events.

35. The antitachycardia pacemaker of claim 32, including means for restarting treatment by said primary and secondary modalities if the rate of said continuing tachycardia exceeds said selected tachycardia rate for said selected high rate number of events and the events have an onset which exceeds a selected rate of onset or the rate of said continuing tachycardia exceeds said selected tachycardia rate for a selected sustained high rate number of events which exceeds said selected high rate number of events.

36. An antitachycardia pacemaker comprising:
   means for detecting electrical cardiac events occurring in at least one chamber of the heart.
   means for counting a first electrical event if the time interval between the first cardiac event and an immediately preceding event is less than a selected tachycardia time interval, and for counting successive cardiac events following said first event if the time interval between each of said successive events and its immediately preceding event is less than said selected tachycardia time interval and does not vary by more than a selected degree of interval change from a selected rate stability interval,
   means responsive to said counting means for detecting a pace-terminable tachycardia whenever a selected number of events is counted, and
   means responsive to said pace-terminable tachycardia detecting means for pacing the heart to terminate the tachycardia.

37. The antitachycardia pacemaker of claim 36, further including means for defining said rate stability time interval at any particular point in time as the average of a predefined averaging number of cardiac time intervals preceding said particular point in time.

38. The antitachycardia pacemaker of claim 37, including means for defining said averaging number as at least 3.

* * * * *

REEXAMINATION CERTIFICATE (3036th)
United States Patent [19]
Pless et al.

[11] B1 4,880,005
[45] Certificate Issued Oct. 29, 1996

[54] PACEMAKER FOR DETECTING AND TERMINATING A TACHYCARDIA

[75] Inventors: Benjamin D. Pless, Palo Alto; Michael B. Sweeney, Mountain View, both of Calif.

[73] Assignee: Intermedics, Inc., Angleton, Tex.

Reexamination Request:
No. 90/003,758, Mar. 16, 1995

Reexamination Certificate for:
Patent No.: 4,880,005
Issued: Nov. 14, 1989
Appl. No.: 198,614
Filed: May 23, 1988

Related U.S. Application Data

[63] Continuation of Ser. No. 765,047, Aug. 12, 1985, abandoned.

[51] Int. Cl.$^6$ .................................................... A61N 1/362
[52] U.S. Cl. ................................ 607/15; 128/705; 607/30

[56] References Cited

U.S. PATENT DOCUMENTS

| | | | |
|---|---|---|---|
| 4,384,585 | 5/1983 | Zipes | 128/419 |
| 4,406,287 | 9/1983 | Nappholz et al. | 128/419 |
| 4,493,325 | 1/1985 | Hartlaub et al. | 182/419 |
| 4,587,970 | 5/1986 | Holley et al. | |
| 4,595,009 | 6/1986 | Leinders | 128/419 |

FOREIGN PATENT DOCUMENTS 0094758  11/1983  European Pat. Off. .

OTHER PUBLICATIONS

Product Specification, Medtronic Implantable Programmable Cardioverter (internal Medtronic document; Bates numbered VP004327–4331.
Book Published by Teletronics, Chapter 9, 1983.
Program Abstracts, "Literaturzusammenstellung zu anti-tachykarden Schrittmachern", *Deutsche Arbeitsgemeinschaft Herzschrittmacher e.V.*, Mar. 10, 1984.
Herz–Schrittmacher Zeitschrift fur Elektrostimulation in der Kardiologie, *German Journal on Cardiac Pacing*, Mar. 31, 1884.
Zipes et al, "Synchronus Intracardiac Cardioversion", *PACE*, vol. 7, Part II, pp. 522–533, May–Jun., 1994.
Arzbaecher et al., "Automatic Tachycardia Detection And Distinction In Anti–Tachycardia Pacing", *PACE*, vol. 8, Part II, p. A–48, May–Jun., 1985.
Technical Manual, The PCD Tachyarrhythmia Control Device, Model 7216A, Medtronic, Dec. 1988.
Guardian ATP 4210 Implantable Defibrillator/Pacemaker, Telectronics (Bates numbered VP004238–4239).
Arzbaecher, Robert, et al., "Automatic Tachycardia Recognition", May–Jun. 1984, Part II, PACE, vol. 7, pp. 541–547.
Camm, A. J. and Ward, D. E., "Pacing for Tachycardia Control", Telectronics, 1983, pp. 139, (Camm Reference).
Fischer, John D., et al., "Maximal Rate of Tachycardia Development: Sinus Tachycardia with Sudden Exercise vs. Spontaneous Ventricular Tachycardia", Mar.–Apr., 1983, Part I, PACE, vol. 6, pp. 221–227.

*Primary Examiner*—William E. Kamm

[57] ABSTRACT

A heart pacemaker detects pace-terminable tachycardia conditions in the atrium of the heart in accordance with selected high rate, rate stability, sudden onset and sustained high rate criteria. When a pace-terminable tachycardia is detected, programmed treatment modalities are applied to attempt to terminate the tachycardia. The tachycardia is treated by applying timed bursts of electrical pulses in formats defined by programmed primary and secondary treatment modalities. The primary and secondary treatments may be applied in an order which is dependent upon the prior successful treatment of similar tachycardias. The pacemaker may also utilize remembered treatment values which were successfully applied to treat similar tachycardias. The pacemaker may be programmed to restart the primary and secondary modes of treatment in the event that the modes initially failed to terminate a tachycardia. The pacemaker may also be programmed to limit the rate of burst pulses to avoid overstimulating the heart.

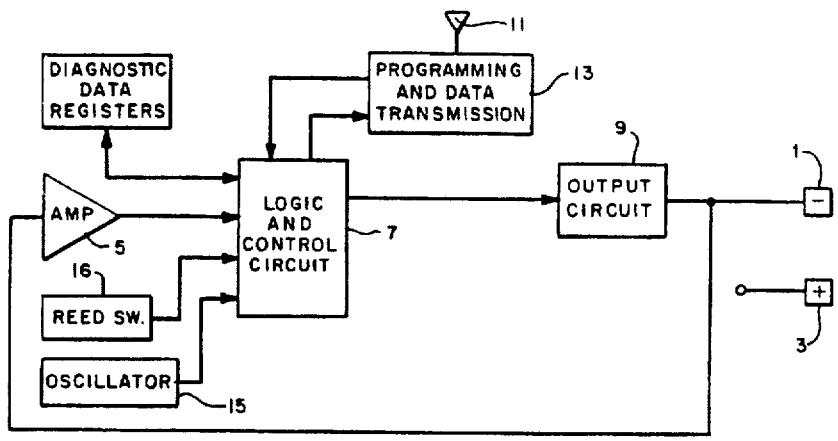

REEXAMINATION CERTIFICATE ISSUED UNDER 35 U.S.C. 307

NO AMENDMENTS HAVE BEEN MADE TO THE PATENT.

AS A RESULT OF REEXAMINATION, IT HAS BEEN DETERMINED THAT:

The patentability of claims 1–38 is confirmed.

* * * * *